United States Patent [19]

Freeland

[11] Patent Number: 4,862,883
[45] Date of Patent: Sep. 5, 1989

[54] INTERLOCKING INTRAMEDULLARY NAIL

[76] Inventor: Yosef Freeland, 11871 Artesia Blvd., Artesia, Calif. 90701

[21] Appl. No.: 184,134

[22] Filed: Apr. 21, 1988

[51] Int. Cl.$^4$ .............................................. A61F 5/04
[52] U.S. Cl. ............................ 128/92 YZ; 128/92 YY
[58] Field of Search ........... 128/92 Y, 92 YZ, 92 YY, 128/92 YK, 92 YN, 92 YV, 92 VD, 92 YF; 411/344, 38, 50

[56] References Cited

U.S. PATENT DOCUMENTS

| 4,227,518 | 10/1980 | Aginsky | 128/92 YP |
| 4,275,717 | 6/1981 | Bolesky | 128/92 YY |
| 4,519,100 | 5/1985 | Wills et al. | 128/92 YY |
| 4,632,101 | 12/1986 | Freeland | 128/92 YY |
| 4,721,103 | 1/1988 | Freeland | 128/92 YY |

FOREIGN PATENT DOCUMENTS

2606269  5/1988  France ............................ 128/92 YF

Primary Examiner—Robert A. Hafer
Assistant Examiner—Charles H. Sam
Attorney, Agent, or Firm—Georges A. Maxwell

[57] ABSTRACT

An intramedullary nail comprising an elongate tubular rod with upper proximal and lower distal ends and positioned within and extending longitudinally of the intramedullary canal of a fractured bone. A pair of adjacent, elongate anchor blades with upper and lower ends are positioned with their upper end portions within a transverse slot in the distal end of the rod and are connected therewith by a single transverse pivot pin. The blades normally extend downwardly from the rod and are pivoted radially outwardly from opposite sides of the rod to deployed positions where they establish anchoring engagement within the bone. The blades have cam parts and stop edges at their upper ends. An elongate setting tool is slidably engaged in and shiftable downwardly in the rod. The tool has a downwardly-disposed surface normally engaging said cam parts to pivot the blades to their deployed positions when the tool is moved downwardly and to establish stopped engagement with said stop edges when the blades are deployed. An elongate anchor screw is engaged transversely through the upper end portion of the bone and is engaged through openings in the rod and the tool to anchor the upper end of the rod in and with the upper end of the bone and to lock the tool in the rod with said surface and edges in stopped engagement. Inserting, guide and reaction tools are provided to facilitate implantation of the device in the bone.

17 Claims, 4 Drawing Sheets

INTERLOCKING INTRAMEDULLARY NAIL

PRIOR ART

| U.S. Patent Documents | | |
|---|---|---|
| 1,269,912 | 6/1918 | Dunham |
| 3,759,257 | 9/1973 | Fischer et al. |
| 3,760,802 | 9/1973 | Fischer et al. |
| 3,779,239 | 12/1973 | Fischer et al. |
| 4,091,806 | 5/1978 | Aginsky |
| 4,204,531 | 5/1980 | Aginsky |
| 4,227,518 | 10/1980 | Aginsky |
| 4,236,512 | 12/1980 | Aginsky |
| 4,275,717 | 6/1981 | Bolesky |
| 4,409,974 | 10/18/83 | Freedland |
| 4,519,100 | 5/1985 | Wills et al. |
| 4,632,101 | 12/30/84 | Freedland |
| 4,721,103. | 1/26/88 | Freedland |

The above-cited Freedland Patents Nos. 4,632,101 and 4,721,103 are the most pertinent of the prior art. Each of the noted Freedland patents discloses an intramedullary nail device including a tubular rod with the deployable strut-like blades pivotally connected with the distal end portion thereof by pivot pins. Those patents further include actuating shafts shiftably related to the rods and coupled with parts of the blades to pivot the blades from undeployed to deployed positions relative to the rod. The notable shortcomings in the noted prior art Freedland devices resides in the fact that the design, disposition and mechanical relationship of the rods, blades, and the pivot pins is such that the parts must be made so small, light or fragile that the devices are likely, in certain cases, to be incapable of withstanding the anticipated forces to which the devices are likely to be subjected to when in use. In other cases, the complicated form of the parts and the relationship of those parts is such that the devices are subject to being rendered inoperable by adverse chemical degradation of the parts in the environment in which they are to be used.

BACKGROUND OF THE INVENTION

In the art of orthopedic surgery, when bones are fractured and/or broken, it is common practice to releasably secure parts and portions of the broken and fractured bones together with specially designed metal hardware and fasteners throughout those protracted periods of time which are required for the bones to mend.

The intramedullary nail structure that I provide is suitable fro use in different bones. For the purpose of this disclosure, I will illustrate and describe it related to the femur bone. The femur is characterized by a central, intramedullary canal that extends throughout the longitudinal extent of the bone. The canal, like the bone itself, has a narrow or small-incross-section, central isthmus portion and large-in-cross-section, longitudinally outwardly divergent, upper and lower end portions.

The femur is a major load-supporting bone which, in use, is subjected to substantial axially-directed compressive loading and is subjected to frequent and substantial torsional loading.

When femurs are fractured and/or broken to an extent that they cannot be effectively immobilized or restrained from excessive movement to enable proper mending thereof by external means, such as casts and the like, it has become common practice to support those bones with elongate, intramedullary rods. The rods are entered into the intramedullary canals through access openings established in the upper ends of the bones. The rods are driven into the bone to extend from one end portion thereof to the other.

To assure that the rods afford maximum and effective support for the bones, they are often fluted longitudinally so that flutes engage the central or isthmus portions of the bones and set the bones against circumferential movement about the exterior of the rods. When the central portions of the bones are in supported engagement with the rods, the rods are most effective to torsionally immobilize parts and portions of the fractured bones which are in supported engagement with the rods and to assure proper mending of the bones. The upper and lower end portions of the rods extend freely through the upper and lower portions of the intramedullary canals of the bones and afford no radial or lateral support for those portions of the bones. As a result, such rods afford little support and are often of marginal effectiveness in the case of breaks and fractures in the upper and lower (one-third) portions of the bones. The above-referred-to prior art rods are not intended and are such that they afford little or no compressive forces directed longitudinally of their related bones.

A newer class of intramedullay rods address and fasten to the proximal and distal end portions of the medullary canals of related bones. Those rods are typically provided with strut-like blades at their lower distal ends. The blades are deployed radially outward relative to the rods to extend through the large lower end portion of the intramedullary canals and to establish anchoring engagement in and with the lower end portions of the bones, after the rods have been positioned within the bones. The upper ends of such rods are commonly fastened to the upper end portions of the bones by anchor screws that are engaged and extend transversely through the rods and their related portions of the bones.

This new class of intramedullary rods are most often tubular parts with extremely this walls and are highly subject to being torsionally deflected to an extent that they are rendered inoperable. Certain of those thin-walled parts are formed with longitudinally-extending slots and the like that further weakens them and in which boney debris tends to collect and works to fowl operation thereof and impede deployment of the blades.

In addition to the above, the deployable blades that the prior art has provided to anchor the lower end of intramedullary rods to related bones are, for one or more obvious and apparent reasons, unstable and such that they afford rather limited and often times inadequate resistance to torsional turning of the rods within and relative to the bones. The above-referred-to prior art blades are, in some instances, established by long, thin, longitudinally-extending, radially-outwardly-deflectable portions of the rods that are deployed by setting tools engaged within the rods and which, upon longitudinal shifting thereof, displace the blades outwardly. Such radially displaced or deflected blades afford little or no torsional support between their related rods and bones. In other instances, due to the limitation of space, the blades must be made so small, thin, light and/or fragile that they cannot be made sufficiently strong and stiff to prevent excessive torsional deflection and/or movement between the blades and their related rods, resulting in excessive torsional movement between the rods and their related bones and detrimental torsional movement and displacement of the fractured bone parts.

OBJECTS AND FEATURES OF MY INVENTION

An object of my invention is to provide an improved, intramedullary nail device which, when set and in use, includes but six parts, each of which is of strong and durable design and size and is in effective, intersupporting engagement with its related parts; and, so that the device, as a whole, is imparted with greater compressive, tensile and torsional strength than is provided by intramedullary nail devices of a similar nature that are known to me to have been provided by the prior art.

It is an object and feature of my invention to provide a nail device of the general character referred to above that includes: (1) an elongate tubular rod with upper proximal and lower distal ends; (2) a pivot pin in the distal end of the rod; (3) a pair of like bone-engaging anchoring blades carried by the pin and the rod; (4) an elongate setting tool engaged within the rod and holding the blades deployed; and, (5) a bone-engaging anchoring screw extending transversely through the proximal end portion of the tube and the setting tool therein.

It is further object and feature of my invention to provide a nail device of the general character referred to above wherein the anchoring blades are pivotally movable about a common fixed turning axis defined by the pivot pin and are in flat, intersupporting engagement with each other and in supported bearing engagement with and between spaced opposing support surfaces defined by blade-receiving notches in the rod.

It is another object and feature of my invention to provide a new nail device of the character referred to above wherein the setting tool includes an elongate shaft that is normally in stopped direct intersupporting engagement with the tube and with the blades.

It is an object and feature of my invention to provide a device of the general character referred to above wherein the anchor screw extends transversely through and is in releasable fixed position relative to a related bone and extends transversely through aligned anchor screw passage in the shaft and appertures in the rod.

It is an object and feature of my invention to provide a device of the general character referred to above wherein the length of the blades can be easily and conveniently adjusted, the depth of the blades is substantially equal to the greater or outside diametric extent of the rod, and the thickness of the blades can be advantageously made substantially equal to greater than one-sixth the outside diameter of the rod; and, a device wherein the diameter of the pivot pin for the blades can be made substantially equal to one-quarter the outside diameter of the rod, whereby the blades and pin are strong, rigid and durable parts.

Another object and feature of the invention is to provide a nail device of the character referred to wherein the blades have cam portions engagable with the lower distal end of said shaft when the blades are undeployed and have straight upper edges that establish stopped engagement with said distal end of the shaft when the blades are deployed.

It is an object and feature of my invention to provide a device of the character referred to above wherein the setting tool is engaged in the rod after the rod is inserted into a related bone in position to deploy the blades and which includes a removable inserting tool with an elongate shaft that engages and maintains the blades undeployed when the device is moved into position within the bone.

A further object of the invention is to provide a device of the character referred to above which includes a manually-engagable guide tool releasably engagable with the proximal end portion of the rod and which includes drill and anchor screw guide bushings to orient and direct a drill into and through the bone, to establish anchor screw pilot openings in the bone that are concentric with anchor screw appertures and a passage in the rod and in the setting tool, and to orient and maintain the anchor screw concentric with said pilot openings, appertures and passage when the screw is advanced into engagement with and through the bone and the device.

It is an object of my invention to provide an intramedullary nail device of the general character referred to above wherein said guide tool is releasably secured to the upper proximal end of the setting tool shaft by a headed bolt; the guide tool includes means engagable with the rod and setting tool to maintain the parts of the construction in predetermined relative rotative position; and, wherein a manually-engagable reaction tool is provided to engage and hold the proximal end of the rod against longitudinal movement and displacement relative to the bone when the setting tool is forcibly moved longitudinally downward therein to deploy said blades.

The foregoing and other objects and features of my invention will be apparent and will be fully understood from the following detailed description of one preferred form and embodiment of the invention, throughout which description reference is made to the accompanying drawings.

DESCRIPTION OF THE DRAWINGS

FIG. 22 is a sectional view of another form of guide tool related to the upper end portion of my nail device assembly;

FIG. 23 is a view similar to FIG. 22 showing the guide tool in another position; and, FIG. 24 is an exploded view of the structure shown in FIG. 23.

DETAILED DESCRIPTION OF THE INVENTION

Figures 1, 2, 3, 4, 5, 6, 7, 8:
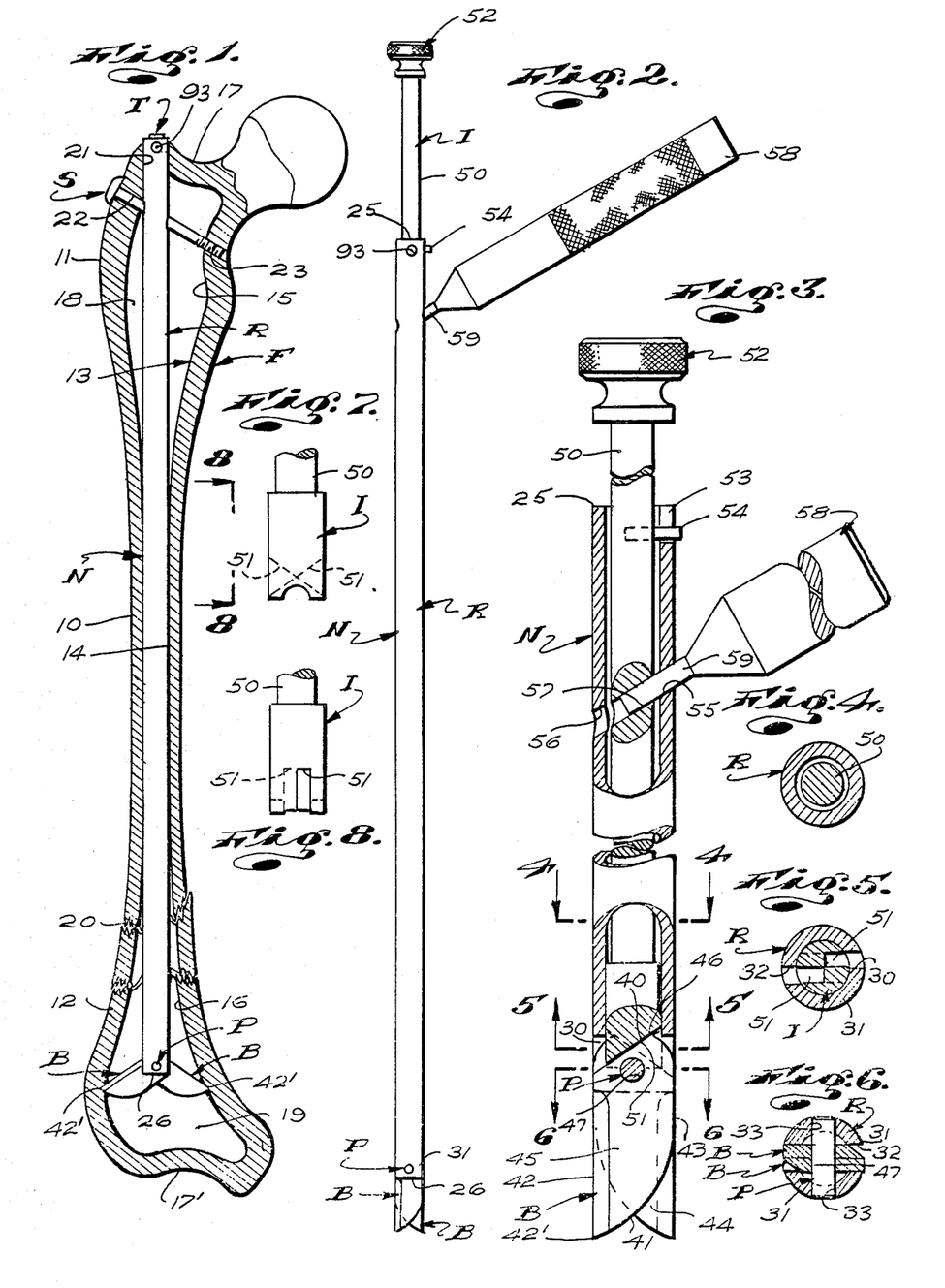
FIG. 1 is a longitudinal sectional view of a fractured femur bone with my new intramedullary nail device set therein.
FIG. 2 is a side elevational view of a portion of my new nail device in an unactuated position and with my new inserting tool engaged therewith.
FIG. 3 is an elongate, detailed sectional view of the structure shown in FIG. 2.
FIG. 4 is a sectional view taken as indicated by line 4—4 on FIG. 3.
FIG. 5 is a view taken substantially as indicated by line 5—5 on FIG. 3.
FIG. 6 is a view taken substantially as indicated by line 6—6 on FIG. 3.
FIG. 7 is an elevational view of the distal end portion of the inserting tool.
FIG. 8 is a view taken substantially as indicated by line 8—8 on FIG. 7.

In FIG. 1 of the drawings, I have shown my new, intramedullary nail device N engaged and set within a fractured femur bone F.

The bone F is an elongate, vertically extending bone with an elongate, narrow isthmus or central portion 10, an elongate, upwardly-projecting and substantially radially outwardly divergent upper or proximal end portion 11, and an elongate downwardly-projecting and substantially radially outwardly divergent lower or distal end portion 12. The longitudinal extend of each of the portions 10, 11 and 12 is equal to about one-third of the overall length of the bone. The bone is tubular in cross-section and defines an intramedullary canal 13 with a narrow isthmus portion 14, an upwardly and radially outwardly divergent upper portion 15, and a downwardly and radially outwardly divergent lower portion 16, each of which portions is co-extensive with the portions 10, 11 and 12 of the bone. The upper end of the canal is closed by the greater irochanter or upper end wall 17 of the bone and the lower end of the canal is closed by the lower end wall 17' of the bone.

The wall thicknesses of the isthmus portion 10 and the portions of the longitudinally inner end portions of the upper and lower portions 11 and 12 of the bone are substantially uniform and rather thin. The wall thickness of the outer end portions of the upper and lower portions 11 and 12 of the bone increase substantially. Accordingly, the opposite end portions of the bone are thick-walled and exceedingly strong while the central portion thereof is relatively thin-walled and weaker than said end portions.

The enlarged end portions 15 and 16 of the canal 13 define enlarged, longitudinally inwardly converging end chambers 18 and 19 within the bone.

In the case illustrated, the lower portion 12 of the bone is shown fractured at 20.

The canal 13 is filled with bone marrow (not shown) which is a rather soft, sponge-like bone material.

In the case illustrated, the upper end wall or irochanter 17 is formed with a vertical access opening 21 by a suitable drilling operation. The opening 21 is substantially concentric with the central longitudinal axis of the bone and/or the canal therein.

An elongate boring and reaming tool (not shown) is entered into the bone, through the opening 21, and is advanced into and through the bone to establish a central rod-receiving passage in and through the marrow and to ream and smooth the inside surface of the isthmus portion of the bone to a predetermined gauge. The foregoing work performed on and within the bone is work that is performed on such bones preparatory to the implantation of intramedullary nail devices therein.

The intramedullary nail device N here provided and which is engaged and set in the bone F includes an elongate, tubular rod R with an upper, proximal end 25 and a lower, distal end 26. The lower, distal end of the rod is releasably fixed to the lower end portion of the bone by a pair of radially outwardly and downwardly projecting deployed anchor blades B that are pivotally carried by a pivot pin P at the lower end portion of the rod. The blades B are locked in set position and are supported by a setting tool T that is engaged within and extends longitudinally through the rod. The blades B project through the bone marrow in the lower chamber 19 of the bone and have tip ends that are engaged and set in anchoring engagement in the wall of the bone, as clearly shown in FIG. 1 of the drawings.

The upper end portion of the rod R is releasably fixed in and with the upper end portion of the bone F by an elongate, anchor screw S. The screw S is engaged in the bone to extend transversely through and across the upper end portion of the bone and extends through the bone marrow in the chamber 18, through anchor screw appertures in the rod R and through an anchor screw passage in the tool T. The bone is provided with an inner anchor screw opening 22 and a threaded outer anchor screw opening 23 established by suitable drilling and tapping operations that are performed subsequent to that time when the rod is in set position in the bone and the blades B have been deployed.

The upper end portion of the rod R is preferably in close bearing engagement with the bone structure defining the access opening 21 in the top wall 17 of the bone and its upper end preferably terminates in close proximity with the upper exterior surface of the bone that occurs adjacent thereto.

The structure that I have thus far described is the basic structure of the intramedullary nail device N that I provide. It will be apparent that the device N includes but six parts, namely the rod R, pivot pin P, the two anchor blades B, the setting tool T, and the screw S. As shown throughout the drawings and as will hereinafter be described in greater detail, the parts of my device, which are metal parts, are of extremely simple design and, more important, they are such that each can be and is made of such size and mass and with such tolerances and/or clearances that each is a strong and durable part. Otherwise stated, the device N is such that no part or portion thereof is necessarily made so small, thin, weak or fragile as to impart the device with any great or apparent weakness.

Considering the device in greater detail and as best shown in Figs. 2 through 6, 14 and 15 of the drawings, the lower end portion of the rod R is formed with a pair of diametrically opposite, elongate, axially downwardly and radially opening blade-accommodating slots 30. The slots 30 define a pair of diametrically opposite, depending legs 31 at the lower end of the rod, between the slots. The slots have or are defined by longitudinally extending, parallel, laterally spaced, opposing blade-engaging edges 32 on the legs 31.

The legs 31 are formed with axially aligned pivot pin openings 33 which occur on a horizontal axis that intersects the central longitudinal axis of the rod and is normal to the mean radial plane of the slots 30. The pivot pin P is engaged in and through the openings 33 to bridge the space between the legs. The outer ends of the pin P are suitably headed or peened so as to support and prevent radial outward deflection or spreading of the legs.

Figures 9, 10, 11, 12, 13, 14, 15, 16:
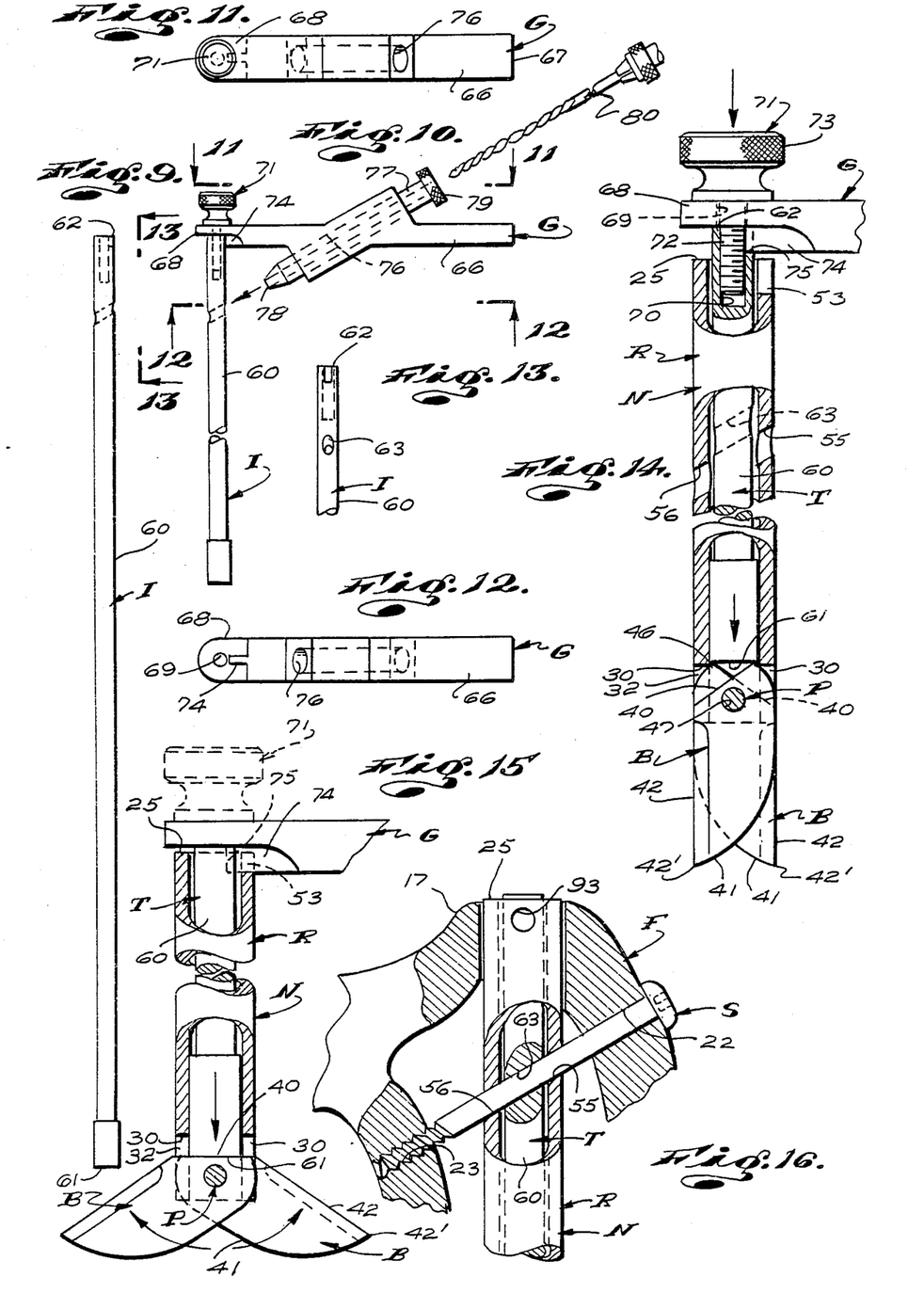
FIG. 9 is a longitudinal view of the setting tool.
FIG. 10 is a view of the setting tool with a guide tool related thereto.
FIG. 11 is a view taken as indicated by line 11—11 on FIG. 10.
FIG. 12 is a view taken as indicated by line 12—12 on FIG. 10.
FIG. 13 is a view taken as indicated by line 12—12 on FIG. 9.
FIG. 14 is an enlarged, detailed sectional view showing parts of the structure in an unactuated position.
FIG. 15 is a view showing parts of the structure in another position.
FIG. 16 is a enlarged, detailed sectional view of a portion of that structure which is shown in FIG. 1.

The blades B are like, elongate, flat, plate-like parts with upper end edges 40, lower end edges 41, straight parallel opposite side edges 42 and 43, and flat inside and outside surfaces 44 and 45. The lateral extent of the blades (between their edges 42 and 43) is preferably equal to the outside diameter of the rod. The thickness of the blades (between the surfaces 44 and 45 thereof) is one-half the lateral extent of the notches 30 in the rod. The side edges 42 are formed to establish sharp cutting edges. The bottom edges 41 are radiused upwardly from the lower ends of the edges 42 to fare smoothly into or with the edges 43. The edges 42 and 41 converge to establish lancet-like points 42' at the lower ends of the edges 42. The top edges 40 extend diagonally between the side edges 42 and 43 at an angle of, for example, thirty-five degrees (35°) and such that when the blades are undeployed, as shown in FIG. 3 of the drawings, and are positioned with their central longitudinal axes parallel with the rod R, the edges 40 are inclined at thirty-five degrees (35°), relative to the axis of the rod. Accordingly, when the blades are deployed to extend radially outward from the rod R at thirty-five degrees (35°), as shown in FIG. 15 of the drawings, the edges 40 extend horizontally and are right angle to the axis of the rod and are disposed upwardly.

The blades are preferably substantially longer than the slots 32 and have upper end portions that occur within the lower end portion of the rod and within the slots 30. The blades have lower end portions that project freely from within the rod and the slots, as shown.

The upper end portions of the side edges 43 of the blades are radiused upwardly and inwardly to converge with the upper end edges 40 to define cam lobes 46 that are disposed upwardly and occur radially inward from the wall of the rod, when the blades are in their undeployed positions.

The upper portions of the blades are formed with pivot pin openings 47 on axes concentric with the radius of the upper end portions of the edges 43.

The blades are arranged with their flat, inner surfaces 44 in flat intersupporting bearing engagement with each other, their pin openings 47 aligned, and with the edges 42 and 43 of one blade disposed oppositely from the direction in which the edges 42 and 43 of the other blade are disposed. The blades, arranged as above noted, are positioned with their upper portions within the notches 30 in the rod, with the pivot pin P in bearing supporting engagement in and through the openings 47, and with their flat, outer surfaces 45 in opposing bearing and intersupporting engagement with their related edges 32 in the slots 30.

Prior to and during implantation of the nail device N, the blades B must be set and maintained in that undeployed position where they are parallel with and depend from the lower end of the rod R. To assure that the blades are maintained in their undeployed position, I provide an inserting tool I that is releasably engaged within the tubular rod R. The tool I is engaged in the rod R prior to that time when the setting tool T is engaged in the rod R and is removed from within the rod when the rod is positioned within the bone F preparatory to deploying the blades and at which time the above-noted setting tool is engaged in the rod.

The inserting tool I includes an elongate, cylindrical shaft 50 with upper proximal and lower distal ends. The shaft is freely shiftable longitudinally in the rod. The lower distal end of the shaft is formed with a pair of adjacent, downwardly and radially outwardly inclined working surfaces 51. Each of the surfaces 51 is parallel with and disposed above the upper end edge 40 of a related blade B. The surfaces 51 are inclined at, for example, thirty-five degrees (35°) relative to the longitudinal axis of the shaft and are inclined oppositely relative to each other so that they are parallel with and oppose the edges 40 of their related blades. When the tool I is fully engaged in the rod R, the surfaces 51 establish linear stopped engagement with the upper end edges 40 of their related blades (as clearly shown in FIG. 3 of the drawings) and effectively maintain the blades in their undeployed positions.

The shaft 50 is preferably substantially greater in longitudinal extent than the rod R so that its upper end portion projects freely upwardly from the upper proximal end of the rod and is manually accessible. The upper end of the shaft 50 can, as shown, be provided with an enlarged, manually engagable head 52.

To facilitate effective and proper alignment of the surfaces 51 with their related edges 40, the upper end of the rod R is provided with an axially upwardly and radially opening orienting notch 53 and the shaft 50 is provided with and carries a radially outwardly projecting orienting pin 54 that normally enters the notch and bottoms-out within the notch when the surfaces 51 and edges 40 are in full stopped engagement with each other. The axes of the notch 53 and pin 54 are on a radial plane that is normal to the plane on which the pivot pin P occurs.

When the rod R and shaft 50 are in set relative axial position and in set relative rotative position, as defined by either or both the slot 53 and pin 54 and the pairs of related edges 40 and surfaces 51, a pair of axially aligned anchor screw appertures 55 and 56 established in opposite inner and outer sides of the rod R (in the upper end portion thereof) and a passage 57 in the upper portion of the shaft 50 are set in axial alignment, as shown in FIG. 3 of the drawings.

To facilitate manual engagement and manipulation of the assembled rod R and tool I, I provide an elongate, manually engagable handle 58. The handle 58 has a stem 59 at one end that projects through the apperture 55 in the rod R and is slidably frictionally engaged in the passage 57 in the shaft, it projects radially outward from the upper end portion of the rod where it is easily and conveniently gripped and can serve to facilitate manipulation of the rod as it is entered into the bone F.

It is to be understood that the handle 58 is not a necessary part. The handle is an auxiliary tool that a physician can use or refuse to use as he sees fit. If a physician elects not to use the handle 58, the passage 57 in the shaft 50 can be eliminated.

While the foregoing is true, it is to be noted that the stem 59 on the handle 58, when engaged through the apperture 55 and into the passage 57, serves to perform the desirable function of releasably maintaining the shaft 50 down in the rod and the related pairs of edges 40 and surfaces 51 in stopped engagement with each other. Accordingly, the inclusion and use of the handle is preferred, even if the handle is not utilized to manipulate the structure with which it is related.

It is to be noted that the handle 58 is engaged with and projects substantially radially from the upper portion of the rod at a substantial distance below the upper end of the rod and will engage and stop at the top wall 17 of the bone F before the rod is fully advanced, downwardly, into set position within the bone. Accordingly, if the handle is utilized, it must be removed when it stops against the bone and before the rod reaches its fully set position therein.

After the handle is removed, further inward movement of the rod, downwardly in the bone, to its set position, is easily effected by tapping or striking the knob 52 at the upper end of the shaft with any suitable hammer or available striking tool or instrument (not shown).

When the rod is moved into set position in the bone F, the tool I is withdrawn from within the rod, releasing the blades for deployment. When the tool I is removed, the setting tool T, which is best shown in FIGS. 9. 10 and 13 through 16 of the drawings, is entered into the rod.

The setting tool T includes an elongate, cylindrical setting and reinforcing shaft 60 with upper proximal and lower distal ends. The shaft 60 is freely slidably entered into the upper end of the rod R and is shifted axially downwardly therein. The lower distal end of the rod defines a flat, horizontal, downwardly disposed, stop surface 61 that engages the cam lobes 46 at the upper ends of the undeployed blades B when the tool T is initially put into what will be referred to as its upper operating position within the rod R (as clearly shown in FIG. 14 of the drawings).

When in its upper operating position, the upper proximal end of the shaft 60 terminates a limited predetermined distance above the upper proximal end 25 of the rod. That noted distance is substantially equal to the distance the shaft 60 is moved downwardly within the rod R when the tool T is moved from its upper, operated position to a lower, set position where the blades B are deployed (as clearly shown in FIG. 15 of the drawings). When in its lower, set position, the upper proximal end 62 of the shaft 60 is near or substantially flush with the upper proximal end of the rod R, which end of the rod is preferably substantially flush with its adjacent top surface of the bone F.

Finally, the tool T includes a laterally extending anchor screw passage 63 in the upper end portion of the rod 60. The passage 63 is aligned and in register with the anchor screw appertures 55 and 56 in the upper end of the rod, when the whole of the structure is in set position.

With the basic setting tool structure set forth above, after it is positioned within the rod R in its noted upper operating position, its upper proximal end 62 is carefully pressed and/or struck downwardly within the rod by means of a hammer tool. As the shaft is moved downwardly in the rod, the surface 61 at its distal end acts upon the cam lobes 46 of the blades B and pivots the blades radially outward and upward about the pivot pin P and relative to the rod to a fully deployed and set position where the lower tip or pointed ends 42' of the blades are forcibly entered into and establish anchored engagement in the adjacent portions of the wall of the bone F (see FIG. 1 of the drawings).

When the blades B are fully deployed, the surface 61 of the tool T establishes flat, linear, stopped engagement with the straight, horizontal upper end edges 40 of the blades B (as clearly shown in FIG. 15 of the drawings).

When the blades B are fully deployed, they extend radially outwardly and downwardly from the lower end of the rod R at an angle of thirty-five degrees (35°), which is complimentary with the angle of the edges 40 relative to the longitudinal axis of the blades.

When the shaft 60 of the tool T is in its lower, set position, the passage 63 in the shaft registers with the appertures 55 and 56 in the rod and the above-mentioned anchor screw S in engaged in and through the registering passage and appertures to effectively lick the shaft within the rod, in its noted set or actuated position.

When the shaft 60 of the tool T is in its set or actuated position, the surface 61 and edges 40 function to lock the blades B in deployed rotative position on and relative to the pin P in such a manner that pivotal movement of the blade relative to said pin and/or relative to the rod R is prevented.

It is to be particularly noted that the tool T is an element or part of my intramedullary nail device N and is let to remain in the rod so long as the device is left implanted in the bone F.

while the operation and use of the tool T to deploy and set the blades B might be carried out without the aid and use of additional special tools and means, I have determined that certain additional tools and means to facilitate implantation of my nail device N is preferred.

I have determined that the provision of an appropriate means to orient and align the passage 63 in the rod 60 with the appertures 55 and 56 in the rod R is highly desirable. Further, the provision of guide means for aligning suitable drills and a top with the noted passage and appertures and to establish appropriate anchor screw openings in the bone, aligned with said passage and appertures; and, means for guiding the anchor screw S into and through the several aligned openings, appertures and passage, is desired for most effective, efficient and satisfactory implantation of my nail device N.

It is to be noted at this time that the anchor screw S that I provide serves to anchor the upper proximal end portion of the device N in and with the bone F. The screw holds the devices against both axial and torsional movement relative to the bone. The screw S in engaged in and extends transversely through the upper end portion of the bone F, through the rod R and through the shaft 60 of the device N as clearly shown in FIGS. 1 and 16 of the drawings. In practice, the screw is preferably laterally inwardly and axially downwardly inclined relative to the central longitudinal axis of the nail device and the bone, as shown. The screw is inclined as noted so that it is effectively engaged in and through those normally laterally inwardly and outwardly disposed side portions of the bone having great wall thickness and that afford great structural support for the screw.

In accordance with the above, I provide a manually engagable guide too G releasably engagable with the upper proximal end of the setting tool T in predetermined rotative position relative thereto and shiftable axially into and out of rotary locked engagement with the rod R in predetermined rotative position relative thereto.

The guide tool G includes a normally substantially horizontally disposed, elongate, manually engagable handle 66 with an inner end and an outer free end 67. The handle projects radially outward from the central longitudinal axis of the device N. The inner end of the handle is formed with a flat, horizontal, radially inwardly projecting tongue 68 with upwardly and downwardly disposed upper and lower surfaces and which extends across the upper end 62 of the shaft 60 of the tool T with its lower surface in supported engagement therewith. The tongue has a vertical through-opening 69 that is in register with a central, vertical threaded opening 70 established in the upper end portion of the shaft 60. The tongue of the handle is releasably secured to the shaft by a manually engagable headed bolt 71, the shank 72 of which extends through the opening 69 and into the opening 70 and the head 73 of which engages the top surface of the tongue. The head 73 is manually engagable to effect its release and removal, and it also serves as as an anvil that can be advantageously struck with a hammer tool or the like when the structure is operated to effect deployment of the blades, as noted in the preceeding.

The tongue 68 is formed with a radially extending, downwardly projecting, flange-like key 74 that is entered into a radially and axially upwardly opening notch or key-way 75 established in one side of the shaft 60 at the upper end thereof. The key 74 is also engagable in the orienting notch 53 in the upper end of the rod R when the shaft 60, with the tool G related to it, is moved downwardly from its upper, operating position to its lower, set position within the rod R. The key-way 75 is on the same radial plane as the orienting notch 53 with respect to the anchor screw passage 63 in the shaft and the appertures 55 and 56 in the rod. With the tool G set forth above, it will be apparent that the tongue of that tool, in cooperation with the key-way 75 and the notch 53, effectively orients and sets the passage 63 in alignment with the appertures 55 and 56 when the tool T is in its set position.

In addition to the above, the handle 66 is formed with an elongate, radially inwardly and downwardly inclined guide opening 76. The opening 76 occurs radially outward of and in spaced, working relationship from the nail device N and from the bone F in which the nail device is engaged. The guide opening 76 is shown engaged within an enlargement or protuberance in the central portion of the handle. The protuberance has a radially inwardly and downwardly disposed inner end face that occurs beneath the handle and a radially outwardly and upwardly disposed outer face that occurs above the handle. The inner and outer ends of the opening 76 open at said faces on the handle. The guide opening 76 is such that it is axially aligned with the passage 63 and with the appertures 55 and 56 when the setting tool in in its lower set position in the rod and when the blades B are fully deployed.

The guide tool G next includes a pair of similar elongate, tubular guide bushings 77 with inner and outer ends 78 and 79. One bushing has a centrally, longitudinally-extending drill bit opening while the other bushing has a slightly larger tap and drill bit opening. But for the difference in the size of the openings, the bushings 77 are alike. Accordingly, I have elected to illustrate but one of those bushings in the accompanying drawings. The bushings 77 are are selectively slidably engaged in and are shiftable longitudinally within the guide opening 76. The inner ends 78 of the bushings project from below the handle 66 and can be formed to define a sharp, annular cutting edge. The bushings are shiftable longitudinally in the opening 76 to shift the annular cutting edge into and out of engagement or into close working relationship with the exterior surface of the bone F. The outer ends of the bushing are defined by radially outwardly projecting, manually engagable flanges that occur above the handle and facilitate manual movement thereof relative to the handle. The diameter of the opening in one bushing is of suitable gauge to effectively guide an elongate, twist drill 80 or other appropriate boring tool, to drill into and establish inner and outer pilot openings in the bone F.

After the pilot openings are established in the bone F, the first or one bushing 77 is removed from the handle and it is replaced by the second or other bushing 77. Thereafter, a larger drill bit corresponding to the diameter of the shank of the screw S in engaged through the second bushing and the inner pilot opening is enlarged to establish the previously-referred-to inner screw opening 22. Thereafter, a tap is engaged in and through the second bushing to tap the outer pilot opening in the bone and establish the previously-referred-to outer threaded screw opening 23.

Figures 17, 18:
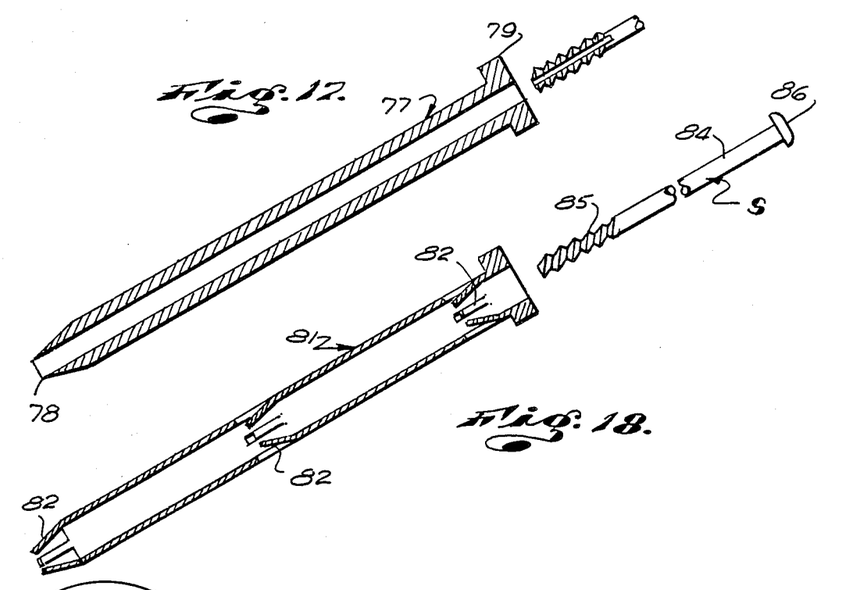
FIG. 17 is a enlarged, detailed sectional view of my new drill pilot bushing.
FIG. 18 is an enlarged, detailed sectional view of my new anchor screw pilot bushing.

In practice, if desired, after the openings 22 and 23 are established in the bone, the second bushing 80 is replaced by an elongate, tubular anchor screw guide bushing 81 (see FIG. 18 of the drawings). The screw guide bushing 81 is similar to the drill guide bushings 77 but has a larger inside diameter to accommodate the head of the anchor screw S and includes a plurality of radially and axially spaced, resilient screw shank engaging and centering fingers 82. The fingers 82 support and guide the shank of the screw concentric with the central longitudinal axis of the bushing and are such that, as the screw is advanced through that bushing, the fingers are yieldingly displaced radially outward by the head of the screw. The bushing 81 is established of thin-walled, resilient metal tube stock and the fingers 82 are established therein by a simple piercing and forming operation.

With the tool G and its related bushings 77 and 81, it will be apparent that the anchor screw openings 22 and 23 in the bone can be easily and accurately established as required and that the anchor screws can be easily and accurately guided and advanced into proper and predetermined engagement in and through the bone and the nail device.

After the screw is engaged in the bone and through the device D and implantation of the device is completed, the bolt 71 and handle G are removed from engagement with the device N.

The anchor screw S can vary in details and design and is shown as a simple form of screw fastener with an elongate, cylindrical shank 84 with inner and outer ends. The outer end portion of the shank 84 is threaded as at 85, and the inner end of the shank is formed with an enlarged head 86. The threaded portion is preferably little greater in longitudinal extend than the depth or axial extent of the threaded outer opening 23 and so that little excess thread is presented that might otherwise be subject to adverse chemical degradation or become impacted in growing bone material. The diameter of the shank portion of the screw S is preferably such that it establishes sliding, bearing-supported engagement with that structure which defines the several openings, appertures and passage, in and through which it extends.

Finally, and in furtherance of my invention, it is likely that the upper end of the setting tool T will have to be struck with substantial force to effect full deployment of the blades B and that, when so struck, the tool T is likely to drive the rod R downwardly in the bone F beyond its desired set position therein. For these occasions when downward displacement of the rod is apt to occur, I provide a manually operable, forcep or tonglike reaction tool H to engage the upper end portion of the rod R and to enable a physician to hold the rod R up and in set position as the tool T is struck and driven downwardly therein.

Figures 19, 20, 21:
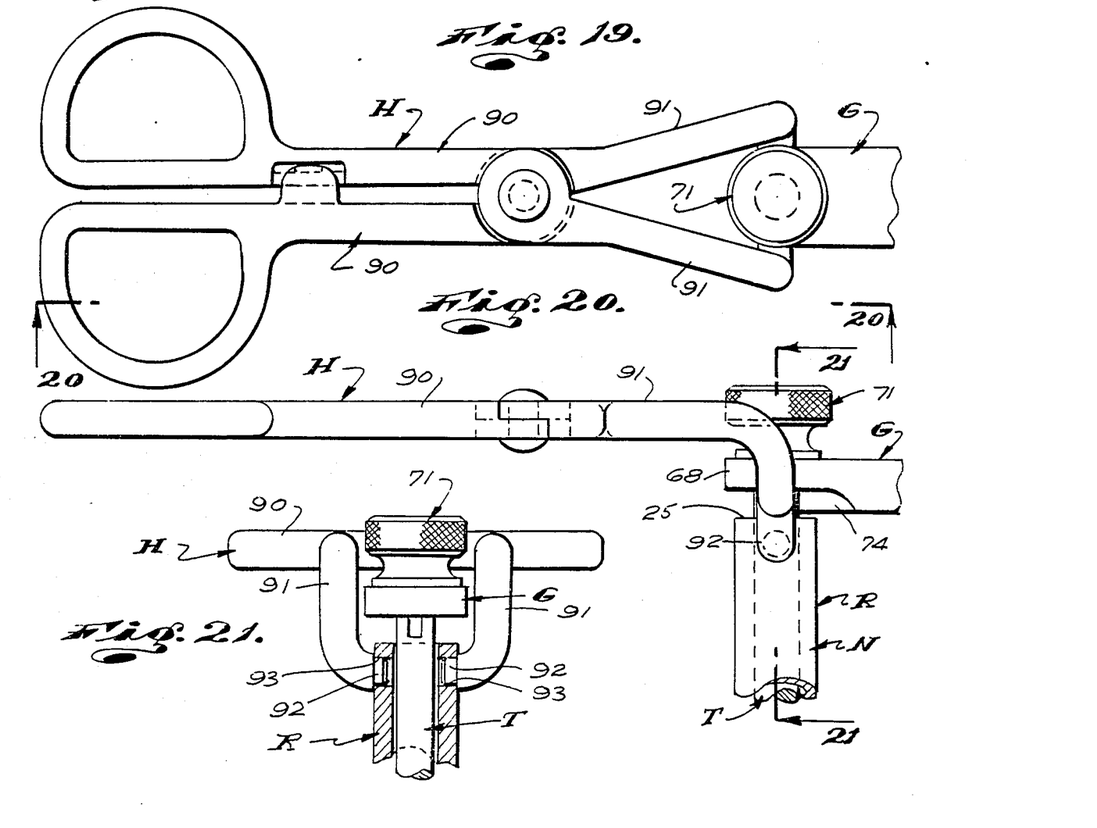
FIG. 19 is an elevational plan view showing my new reaction tool engaged with my nail device.
FIG. 20 is a view taken as indicated by line 20—20 on FIG. 19.
FIG. 21 is a view taken as indicated by line 21—21 on FIG. 20.

Referring to FIGS. 19 through 21 of the drawings, the tool H is a simple scissors-like forceps device including pivotally connected, manually engagable, elongate outer lever arms 90 (with finger loops) and elongate, longitudinally inwardly and downwardly and thence laterally inwardly turned nibs 91 with laterally inwardly projecting trunions 92 at their terminal ends. The upper end portion of the rod is formed with a pair of diametrically oppositely disposed trunion-receiving openings 93. It will be apparent that when it is desired to hold the rod R up, while driving the tool T down, a surgeon can, with one hand, operate the tool H to engage and hold the rod R up, while, with his other hand, strike the upper end of the tool T down, relative to the rod, by means of a suitable hammer tool (not shown).

As an alternative to the use of a hammer or striking tool, a simple, elongate, U-shaped, "gear puller" like tool might employed to move the setting tool T down in the rod R from its operating position to its set position. If such a gear-pulling tool is employed, it is only necessary that the lower ends of the legs of the tool be provided with trunions that can be entered into building engagement in the trunion openings in the rod R. When such a gear-pulling tool is employed, the central, axially downwardly projecting screw part thereof is engaged with the top of the bolt 71 or can be engaged with the upper proximal end 62 of the shaft 60. When and if such a gear-puller-type tool is provided and used, the nail device is screw-driven to its actuated position and there is little or no likelihood that the device might be inadvertently displaced.

Figures 22, 23, 24:
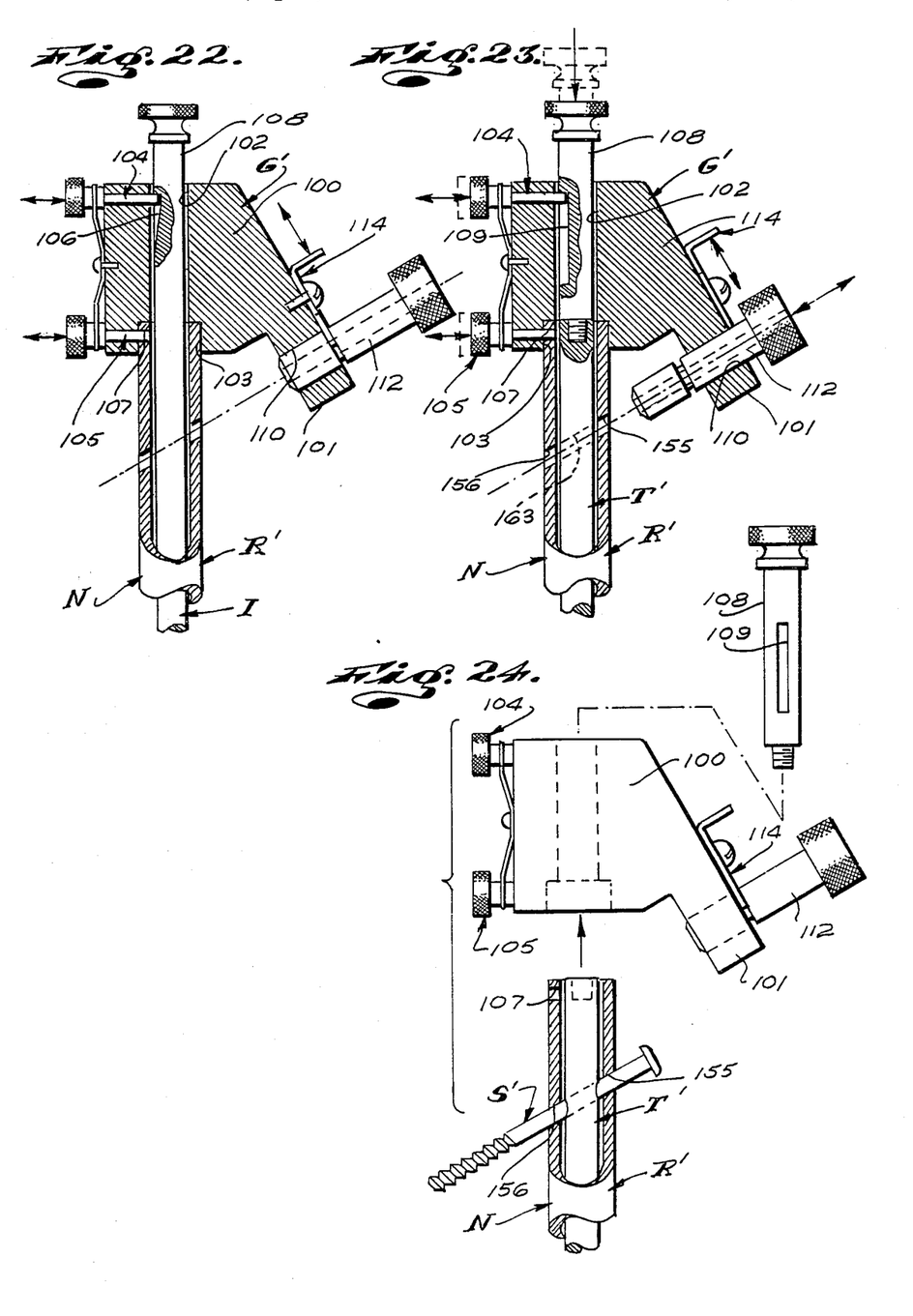

In FIGS. 22, 23 and 24 of the drawings, I have illustrated my last-to-be-developed and preferred guide tool G'. The tool G' includes a blocklike body 100 with upper and lower sides or ends; inwardly and outwardlydisposed front and rear sides and oppositely-disposed lateral sides. The body has a laterally inwardly and downwardly projecting, manually-engagable projection or handle 101. The lower end portion of the handle 101 extends below the bottom of the body.

The body has a vertically extending through-opening 102 selectively freely receiving the upper end portions of the inserting tool I' and setting tool T' of the nail device N' and has a downwardly opening 102. The counterbore releasably slidably receives the upper end portion of the rod R'.

The body carries upper and lower, horizontally disposed, elongate, spring-loaded, manually operable latch pin devices 104 and 105. The latch pins of the devices 104 and 105 normally project into the opening 102 and the bore 103 as clearly shown in FIGS. 22 and 23 of the drawings.

The upper end portion of the inserting tool I' has a manually outwardly disposed longitudinally-extending, latch pin channel 106. The channel 106 has an outwardly and downwardly inclined pin cam surface and an upper latch pin engaging stop end. The pin of the device 104 normally enters the channel 106, rotatably orients the tool I' and stops that tool in set axial or longitudinal position in the rod and relative to the blades (not shown) as the lower end of the rod. Because of the cam surface in the channel 106, the tool I' can be manually withdrawn, upwardly, from engagement in the rod R' and the tool g' without having to manually release the latch device 104.

The pin of the lower latch device 105 normally enters a latch pin opening 107 in the upper end of the rod R' as clearly shown in FIGS. 22 and 23 of the drawings. The latch pin device 105 releasably holds the rod R' engaged in the tool G' with the rod in predetermined rotatative position relative to the tool G'. Upon release of the latch means 105, the tool g' is released from the rod R', as shown in FIG. 24 of the drawings.

The opening 107 in the rod R' is substantially similar to the notch 53 in the rod R as regards circumferential orientation of the parts of the structure and further serves to releasably retain the rod R' and the tool G; coupled. In all other respects, the rod R' and tool I' are identical with the rod R and tool I previously described.

The lower portion of the setting tool T' is identical with the lower end portion of the tool T.

The upper end portion of the tool T' that projects upwardly from the upper end of the rod R' when the nail device N is in its set position is made a separate part that is releasably threadedly engaged into the upper end of and coupled with the remaining lower portion of the tool T' that occurs within the rod R' when the nail device is in set position and as is clearly shown in FIGS. 23 and 24 of the drawings. That is, the setting tool T', unlike the setting tool T which is a unitary part, is sectional and is characterized by a lower primary part or section and an upper, releasable part or section 108.

The section 108 of the tool T' is normally in predetermined set rotative position relative to the lower part or section of that tool and has a longitudinally extending, radially outwardly opening orienting channel 109 in which the pin of the upper latch device 104 is removably engaged when the tool T is initially engaged in the rod R', preparatory to setting the nail device N in a related bone. The device 104 must be manually operated to effect engagement of the pin thereof in the channel 109. When the tool T' is first engaged through the tool G' and into the rod R', it is in an elevated position and is such that it must move down in and relative to the tool G' and the rod R' to a lower, set position in the course of setting the nail device. The device 104 and channel 109 allow for the required downward, longitudinal or axial movement of the tool T' while maintaining the tool T' in set rotative position relative to the tool G' and the rod R'.

The projection or handle 101 of the tool G', like the handle of the tool G, has a guide bushing opening 110 similar to the guide bushing opening 76 in the tool G. Drill bit and tap guide bushings 112 are selectively slidably engaged in the opening 110. The bushing or bushings 112 are similar to the bushings 77 provided in the first embodiment of the guide tool G described in the foregoing.

In this preferred embodiment of my invention, a manually operable latch means 114 is provided to releasably hold the bushings 112 engaged in the handle of the tool G' in a manner to assist manipulation and operation of the structure.

The bushings 112 are aligned with the anchor screw appertures 155 and 156 and the anchor screw opening or passage 163 in the rod R' and tool T'. The noted appertures and passage in this embodiment of my invention are the same as in the first embodiment of my invention.

With the tool G' illustrated and described in the foregoing, after the blades of the nail device N' have been deployed and the upper portion of the device is screw-fastened to its related bone (not shown) by a screw fastener S' engaged through the openings or appertures 155 and 156 and the opening or passage 163, the upper latch device 104 is released and the upper section of the tool T' is unscrewed and separated from the lower section of that tool. Thereafter, the lower latch means 105 is manually released and the tool G' is removed from engagement with the rod R', as clearly shown in FIG. 24 of the drawings.

It will be apparent that the tool G', in effect, integrates the various parts and portions of the first-described guide tool G and its associated elements and parts, into a more compact, desirable and easier-to-operate structure.

A comparison of the two forms of guide tools G and G' that I have illustrated and described makes it apparent that the guide tool or tools that can be provided to effect desired operation and use of my new nail device can be varied widely in form and construction without departing from the broader aspects and spirit of my invention.

After the fractured and/or broken bone F in which the nail device N has been implanted has mended, the device is easily and conveniently removed from engagement within the bone by first removing the screw S and thereafter withdrawing the setting tool T from within the rod R. When the tool T is removed from the rod R, the blades B are left free to pivot downwardly and inwardly from their deployed position to their normal, undeployed position. With the tool T removed from the rod, the upper end of the rod is engaged in the bone. As the rod moves upwardly, the blades pivot substantially freely from their deployed to undeployed positions.

Having described preferred forms and embodiments of my invention, I do not wish to be limited to the specific details herein set forth but wish to reserve to myself any modifications and/or variations that might appear to those skilled in the art and which fall within the scope of the following claims.

Having described my invention, I claim:

1. An intramedullary nail device comprising an elongate vertically extending tubular rod with a side wall having radially outwardly disposed front and rear sides and opposite radially outwardly disposed lateral sides, an open upper end and an open lower end, a downwardly and radially forwardly and rearwardly opening slot extending longitudinally upwardly from said lower end and defining laterally spaced legs with laterally inwardly disposed bladesupporting surfaces, an elongate horizontal laterally extending pivot pin extends transverse the slot and has opposite ends in supported engagement with said legs, a pair of elongate anchor blades each having a central longitudinal axis, upper and lower ends, a flat laterally inwardly disposed inner bearing surface, a flat laterally outwardly disposed outer bearing surface, forwardly and rearwardly disposed longitudinal edges, a lateral pivot pin opening in its upper end portion, a lower end edge converging with a longitudinal edge and defining a bone-engaging lancet point, a straight upper stop edge inclined transversely relative to the longitudinal axis of the blade and having a lower end converging with one longitudinal edge and an upper end converging with the other longitudinal edge and defining an upwardly disposed cam lobe, the blades are arranged in juxtaposition with their inner bearing surfaces in intersupporting engagement with each other, the upper end portions of the blades are positioned within said slot and between said legs with their outer bearing surfaces in interengagement with the supporting surfaces of their related legs and with the pivot pin in rotary engagement in the pivot pin openings, the blades are normally in an unactuated operating position where their axes are parallel with the longitudinal axis of the rod and are pivotally movable to an actuated set position where they are deployed longitudinally downwardly and laterally outwardly relative to the axis of the rod, the upper stop edges of the pair of blades are angularly disposed oppositely relative to the axis of the rod when the blades are in their operating position and are parallel with each other and extend horizontal transverse the axis of the rod when the blades are in set position; an elongate setting tool with upper and lower ends is removably slidably engaged in the rod and is shiftable longitudinally therein from a normal unactuated upper position to a lower actuated set position, the tool has a downwardly disposed working surface engaging the cam lobes when the tool is moved downwardly from its operating position towards its set position and establishes stopped engagement with the stop edges when it is in its set position; and elongate anchor screw removably engaged transversely through a bone within which the device is implanted is removably engaged transversely through registering anchor screw appertures in the rod spaced between the upper and lower ends thereof and through an anchor screw passage in the setting tool that registers with said appertures when the tool is in its set position.

2. The device set forth in claim 1 wherein the forwardly disposed longitudinal edge of one blade converges with the lower end of the inclined stop edge and with the bottom edge to define the lancet point on the blade and the rearwardly disposed longitudinal edge of the other blade converges with the lower end of the inclined stop edge and the bottom edge to define the lancet point on the blade.

3. The device set forth in claim 1 which further includes an elongate manually engagable guide tool with inner and outer ends, the guide tool is positioned with its inner end adjacent to the upper end of the setting tool and is releasably fastened thereto to project radially outwardly from the setting tool and the rod, orienting means is provided between the guide tool and the rod and sets the guide tool in predetermined rotative position relative to the rod, said guide tool has a guide opening spaced radially outward from and in axial alignment with said appertures and passage, said guide opening guides a drill bit in and through said apperture and passage to establish anchor screw pilot openings in and through a bone in which the device is implanted and guides said anchor screw into and through said appertures and passage and into and through anchor screw pilot openings in the related bone.

4. The device set forth in claim 1 which further includes an elongate manually engagable guide tool with inner and outer ends, the guide tool is positioned with its inner end adjacent to the upper end of the setting tool and is releasably fastened thereto to project radially outwardly from the setting tool and the rod, orienting means is provided between the guide tool and the rod and sets the guide tool in predetermined rotative position relative to the rod, said guide tool has a guide opening spaced radially outward from and in axial alignment with said appertures and passage, said guide opening guides a drill bit in and through said apperture and passage to establish anchor screw pilot openings in and through a bone in which the device is implanted and guides said anchor screw into and through said appertures and passage and into and through anchor screw pilot openings in the related bone, the guide tool includes an elongate drill bit bushing selectively engagable in and through the guide opening and an anchor screw bushing selectively engagable in and through the guide opening.

5. The device set forth in claim 1 which further includes an elongate manually engagable guide tool with inner and outer ends, the guide tool is positioned with its inner end adjacent to the upper end of the setting tool and is releasably fastened thereto to project radially outwardly from the setting tool and the rod, orienting means is provided between the guide tool and the rod and sets the guide tool in predetermined rotative position relative to the rod, said guide tool has a guide opening spaced radially outward from and in axial alignment with said appertures and passage, said guide opening guides a drill bit in and through said apperture and passage to establish anchor screw pilot openings in and through a bone in which the device is implanted and guides said anchor screw into and through said appertures and passage and into and through anchor screw pilot openings in the related bone, said orienting means includes an upwardly and radially opening orienting notch in the rod and a radially extending key on the guide tool engaged in the orienting notch.

6. The device set forth in claim 1 which further includes an elongate manually engagable guide tool with inner and outer ends, the guide tool is positioned with its inner end adjacent to the upper end of the setting tool and is releasably fastened thereto to project radially outwardly from the setting tool and the rod, orienting means is provided between the guide tool and the rod and sets the guide tool in predetermined rotative position relative to the rod, said guide tool has a guide opening spaced radially outward from and in axial alignment with said appertures and passage, said guide opening guides a drill bit in and through said apperture and passage to establish anchor screw pilot openings in and through a bone in which the device is implanted and guides said anchor screw into and through said appertures and passage and into and through anchor screw pilot openings in the related bone, said orienting means includes an upwardly and radially opening orienting notch in the rod and a radially extending key on the guide tool engaged in the orienting notch, the guide tool includes an elongate drill bit bushing selectively engagable in and through the guide opening and an anchor screw bushing selectively engagable in and through the guide opening.

7. The device set forth in claim 1 which further includes an elongate manually engagable guide tool with inner and outer ends, the guide tool is positioned with its inner end adjacent to the upper end of the setting tool and is releasably fastened thereto to project radially outwardly from the setting tool and the rod, orienting means is provided between the guide tool and the rod and sets the guide tool in predetermined rotative position relative to the rod, said guide tool has a guide opening spaced radially outward from and in axial alignment with said appertures and passage, said guide opening guides a drill bit in and through said apperture and passage to establish anchor screw pilot openings in and through a bone in which the device is implanted and guides said anchor screw into and through said appertures and passage and into and through anchor screw pilot openings in the related bone, the setting tool has an upwardly opening threaded bolt opening and a radially and axially upwardly opening orienting key-way in its upper end, said guide tool has a vertical bolt opening aligned with the threaded opening and an orienting key engaged in the key-way, a manually engagable bolt is engaged through said bolt opening and into said threaded opening and releasably secures the guide tool to said setting tool.

8. The device set forth in claim 1 which further includes an elongate manually engagable guide tool with inner and outer ends, the guide tool is positioned with its inner end adjacent to the upper end of the setting tool and is releasably fastened thereto to project radially outwardly from the setting tool and the rod, orienting means is provided between the guide tool and the rod and sets the guide tool in predetermined rotative position relative to the rod, said guide tool has a guide opening spaced radially outward from and in axial alignment with said appertures and passage, said guide opening guides a drill bit in and through said apperture and passage to establish anchor screw pilot openings in and through a bone in which the device is implanted and guides said anchor screw into and through said appertures and passage and into and through anchor screw pilot openings in the related bone, the setting tool has an upwardly opening threaded bolt opening and a radially and axially upwardly opening orienting key-way in its upper end, said guide tool has a vertical bolt opening aligned with the threaded opening and an orienting key engaged in the key-way, a manually engagable bolt is engaged through said bolt opening and into said threaded opening and releasably secures the guide tool to said setting tool, said orienting means includes an upwardly and radially opening orienting notch in the rod in which the key on the guide tool is engaged.

9. The device set forth in claim 1 which further includes an elongate manually engagable guide tool with inner and outer ends, the guide tool is positioned with its inner end adjacent to the upper end of the setting tool and is releasably fastened thereto to project radially outwardly from the setting tool and the rod, orienting means is provided between the guide tool and the rod and sets the guide tool in predetermined rotative position relative to the rod, said guide tool has a guide opening spaced radially outward from and in axial alignment with said appertures and passage, said guide opening guides a drill bit in and through said apperture and passage to establish anchor screw pilot openings in and through a bone in which the device is implanted and guides said anchor screw into and through said appertures and passage and into and through anchor screw pilot openings in the related bone; and a reaction tool selectively releasably engagable with the upper end of the rod to hold the rod up when the setting tool is moved downwardly therein from its operating position to its set position, said reaction tool is a scissors-type forceps tool with pivotally related manually engagable lever arms having work-engaging nibs, said nibs have opposing relatively movable trunions, said rod has oppositely disposed trunion-receiving openings in its upper end portion in which the trunions are selectively removably engaged.

10. The device set forth in claim 1 which further includes an elongate inserting tool cooperatively related to the sub-assembly comprising the rod, pivot pin and blades prior to engagement of said setting tool therewith, said inserting tool is selectively removably engaged within the rod and has a pair of straight retaining surfaces angularly related to the longitudinal axis of the tool and each establishing linear engagement with the upper stop edge of a related blade when the blades are in their unactuated operating position, the inserting tool has a transverse stem-receiving passage in axial alignment with the appertures in the rod and a manually engagable stem is removably engaged in and through an apperture and into the stem-receiving passage and releasably locks the inserting tool with said retaining surfaces engaged with said stop surfaces.

11. An intramedullary nail device comprising an elongate vertically extending tubular rod with front, rear and lateral sides, upper and lower ends, a downwardly, forwardly and rearwardly opening slot at said lower and and defining laterally spaced legs with laterally inwardly disposed blade-supporting surfaces, a pivot pin extends transverse the slot and in supported engagement with said legs, a pair of elongate anchor blades each having a central longitudinal axis, upper and lower ends, flat laterally inwardly and outwardly disposed longitudinal edges, a pivot pin opening in its upper end portion, a lower edge converging with a longitudinal edge and defining a bone-engaging lancet point, a straight upper stop edge inclined transversely relative to its longitudinal axis and converging with one longitudinal edge and at an upwardly disposed cam lobe, the blades are arranged with their inner bearing surfaces interengaged, the upper end portions of the blades are positioned within said slot with their outer bearing surfaces engaged with the supporting surfaces of their related legs and with the pivot pin engaged in the pivot pin openings, the blades are normally in an operating position where their axes are parallel with the longitudinal axis of the rod and are pivotally movable to a set position where they are deployed longitudinally downwardly and laterally outwardly relative to the axis of the rod, said stop edges are angularly disposed oppositely relative to the axis of the rod when the blades are in their operating position and are normal to the axis of the rod when in set position; a manually engagable guide tool is releasably engaged with the upper end of the rod in predetermined rotative position relative thereto and has a vertical through-bore with a lower end communicating with the upper end of the rod, an elongate vertically extending inserting tool is slidably removably engaged in and through said bore and in and through the rod, said inserting tool has a lower end with retaining surfaces inclined relative to the axis of the blades and in parallel stopped engagement with the stop edges when the blades are in their operating position; an elongate vertically extending setting tool is selectively removably engaged in and through the bore and in and through the rod in place of said inserting tool and is shiftable downwardly from an unactuated position to an actuated position in the rod, the setting tool has a downwardly disposed working surface engaging said cam lobes when it is in its unactuated position and in parallel stopped engagement with said stop edges when it is in its actuated position, the upper end of the setting tool terminates at the upper end of the rod when it is in its actuated position and has a removable extension projecting upwardly through and from the bore, said rod has axially aligned substantially radially oppositely-disposed fastener-receiving appertures in its upper end portion, said setting tool has a fastener receiving passage that is aligned with the appertures when the setting tool is in its actuated position; and, an elongate anchor fastener is selectively removably engaged in and through the appertures and the passage, said fastener has bone-engaging end portions projecting radially outward from the rod, said setting tool and extension are released from the rod and the setting tool when the fastener is engaged therethrough.

12. The nail device set forth in claim 11 which further includes manually releasable upper and lower latch devices carried by the guide tool, the lower latch device engages and releasably secures the guide tool to the upper end of the rod in predetermined rotative position and against relative axial movement, the upper latch device is selectively releasably engaged with the insert tool and the setting tool extension to releasably hold the insert tool in predetermined rotative position and against relative axial movement and to releasably hold the setting tool in predetermined rotative position and for axial movement of the setting tool from its unactuated position to its actuated position.

13. The nail device set forth in claim 11 which further includes manually releasably upper and lower latch devices carried by the guide tool, the lower latch device engages and releasably secures the guide tool to the upper end of the rod in predetermined rotative position and against relative axial movement, the upper latch device is selectively releasably engaged with the insert tool and the setting tool extension to releasably hold the insert tool in predetermined rotative position and against relative axial movement and to releasably hold the setting tool in predetermined rotative position and for axial movement of the setting tool from its unactuated position to its actuated position; said lower latch device includes a latch part shiftable radially into and out of engagement in a radial opening in the upper end of the rod, said upper latch device includes a latch part selectively shiftably radially into and out of engagement in a radially-disposed latch opening in the inserting tool and into and out of engagement in a radially opening longitudinally extending groove in the extension of the setting tool.

14. The nail device set forth in claim 11 wherein the upper end of the setting tool has a vertical upwardly opening threaded opening and the extension has a depending stem threadedly engaged in the threaded opening.

15. The nail device set forth in claim 11 wherein said guide tool has a bushing opening spaced radially outward from the rod and aligned with the appertures, the guide tool further includes elongate tubular drill bit and tap bushings that are selectively slidably engaged in the bushing opening to align elongate drill bits, taps and said bone fastener with the appertures and the passage in the rod and the setting tool.

16. The nail device set forth in claim 11 which further includes manually releasable upper and lower latch devices carried by the guide tool, the lower latch device engages and releasably secures the guide tool to the upper end of the rod in predetermined rotative position and against relative axial movement, the upper latch device is selectively releasably engaged with the insert tool and the setting tool extension to releasably hold the insert tool in predetermined rotative position and against relative axial movement and to releasably hold the setting tool in predetermined rotative position and for axial movement of the setting tool from its unactuated position to its actuated position, the upper end of the setting tool has a vertical upwardly opening threaded opening and the extension has a depending stem threadedly engaged in the threaded opening.

17. The nail device set forth in claim 11 which further includes manually releasable upper and lower latch devices carried by the guide tool, the lower latch device engages and releasably secures the guide tool to the upper end of the rod in predetermined rotative position and against relative axial movement, the upper latch device is selectively releasably engaged with the insert tool and the setting tool extension to releasably hold the insert tool in predetermined rotative position and against relative axial movement and to releasably hold the setting tool in predetermined rotative position and for axial movement of the setting tool from its unactuated position to its actuated position, the upper end of the setting tool has a vertical upwardly opening threaded opening and the extension has a depending stem threadedly engaged in the threaded opening, the guide tool has a bushing opening spaced radially outward from the rod and aligned with the appertures, the guide tool further includes elongate tubular drill bit and tap bushings that are selectively engagable in and through the bushing opening to align elongate drill bits, taps and the bone fastener with the appertures and the passage in the rod and the setting tool.

* * * * *